(12) United States Patent
Krautkramer et al.

(10) Patent No.: US 6,964,803 B2
(45) Date of Patent: Nov. 15, 2005

(54) ABSORBENT STRUCTURES WITH SELECTIVELY PLACED FLEXIBLE ABSORBENT BINDER

(75) Inventors: Candace Dyan Krautkramer, Neenah, WI (US); Russell Paul George, Appleton, WI (US); Kenneth Russell Casson, Greenville, WI (US); Dave Allen Soerens, Neenah, WI (US); Jason Matthew Laumer, Appleton, WI (US); James Hongxue Wang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/427,564

(22) Filed: May 1, 2003

(65) Prior Publication Data

US 2004/0018365 A1 Jan. 29, 2004

Related U.S. Application Data

(63) Continuation-in-part of application No. 10/206,883, filed on Jul. 26, 2002, and a continuation-in-part of application No. 10/324,478, filed on Dec. 20, 2002.

(51) Int. Cl.$^7$ ................................................ B32B 3/04
(52) U.S. Cl. .................... 428/122; 428/105; 428/913; 442/118; 442/119; 442/149; 442/154; 442/156; 442/157
(58) Field of Search ................ 442/118, 119, 442/149, 154, 156, 157; 428/105, 122, 913

(56) References Cited

U.S. PATENT DOCUMENTS

| | | |
|---|---|---|
| 3,617,362 A | 11/1971 | Bemmels et al. |
| 3,951,893 A * | 4/1976 | Gander .................. 524/322 |
| 3,963,605 A | 6/1976 | Seabourn |
| 4,251,643 A | 2/1981 | Harada et al. |
| 4,291,136 A | 9/1981 | Keogh |
| 4,328,323 A | 5/1982 | Keogh |
| 4,343,917 A | 8/1982 | Keogh |
| 4,353,997 A | 10/1982 | Keogh |
| 4,369,289 A | 1/1983 | Keogh |
| 4,408,011 A | 10/1983 | Barnabeo |
| 4,434,272 A | 2/1984 | Keogh |
| 4,440,907 A | 4/1984 | Keogh |
| 4,446,279 A | 5/1984 | Keogh |
| 4,459,396 A | 7/1984 | Yamasaki et al. |
| 4,489,029 A | 12/1984 | Keogh et al. |
| 4,493,924 A | 1/1985 | Rifi |
| 4,526,930 A | 7/1985 | Keogh |
| 4,551,504 A | 11/1985 | Barnabeo |
| 4,575,535 A | 3/1986 | Keogh |
| 4,579,913 A | 4/1986 | Keogh |
| 4,593,071 A | 6/1986 | Keogh |
| 4,676,820 A | 6/1987 | Le Sergent et al. |
| 4,753,993 A | 6/1988 | Keogh |
| 4,767,820 A | 8/1988 | Keogh |
| 4,921,136 A | 5/1990 | Roggenburg, Jr. |
| 4,940,646 A | 7/1990 | Pawlowski |
| 5,047,476 A | 9/1991 | Keogh |
| 5,089,564 A | 2/1992 | Bullen |
| 5,112,919 A | 5/1992 | Furrer et al. |
| 5,145,906 A | 9/1992 | Chambers et al. |
| 5,196,470 A | 3/1993 | Anderson et al. |
| 5,204,404 A | 4/1993 | Werner, Jr. et al. |
| 5,364,382 A | 11/1994 | Latimer et al. |
| 5,389,728 A | 2/1995 | Prejean |
| 5,532,350 A | 7/1996 | Cottrell et al. |
| 5,656,132 A | 8/1997 | Farrington, Jr. et al. |
| 5,853,867 A * | 12/1998 | Harada et al. ............. 428/317.9 |
| 5,859,074 A | 1/1999 | Rezai et al. |
| 5,911,937 A | 6/1999 | Hekal |
| 5,932,668 A | 8/1999 | Friebe et al. |
| 5,961,763 A | 10/1999 | Makoui et al. |
| D420,525 S | 2/2000 | Watson |
| 6,054,523 A | 4/2000 | Braun et al. |
| 6,110,533 A | 8/2000 | Coté et al. |
| 6,300,275 B1 * | 10/2001 | Weir ..................... 502/402 |
| 6,380,298 B2 | 4/2002 | Flautt et al. |
| 6,403,857 B1 | 6/2002 | Gross et al. |
| 6,417,425 B1 | 7/2002 | Whitmore et al. |
| 6,596,402 B2 | 7/2003 | Soerens et al. |
| 6,689,934 B2 * | 2/2004 | Dodge et al. ............. 604/367 |
| 2002/0090453 A1 | 7/2002 | Muthiah et al. |
| 2003/0149413 A1 | 8/2003 | Mehawej |

FOREIGN PATENT DOCUMENTS

| | | |
|---|---|---|
| CA | 756190 | 4/1967 |
| EP | 0 132 910 A2 | 2/1985 |
| EP | 0 705 861 A1 | 4/1996 |
| EP | 0 844 265 A1 | 5/1998 |
| EP | 0 992 252 | 4/2000 |
| EP | 1 013 291 A1 | 6/2000 |
| EP | 1 059 320 A2 | 12/2000 |
| EP | 1 199 059 | 4/2002 |
| WO | 99/57201 | 11/1999 |
| WO | WO 02/053664 A2 | 7/2002 |

* cited by examiner

Primary Examiner—Helen L. Pezzuto
(74) Attorney, Agent, or Firm—Pauley Petersen & Erickson

(57) ABSTRACT

Absorbent structures having controlled liquid intake, distribution and absorption properties include at least one substrate layer and a flexible absorbent binder formed on and bound to the substrate at selected locations. The flexible absorbent binder is selectively formed so as to provide flow channels, regions of higher and lower fluid intake and absorption, dams for preventing fluid leakage, and other desirable features. The absorbent structures are useful in personal care absorbent articles such as sanitary napkins, diapers, training pants, adult incontinence garments and the like.

41 Claims, 7 Drawing Sheets

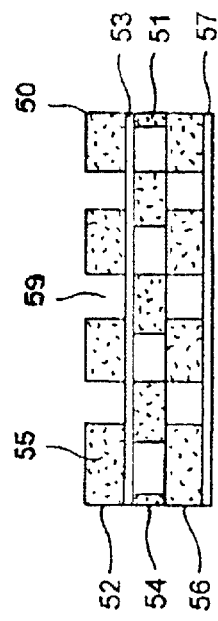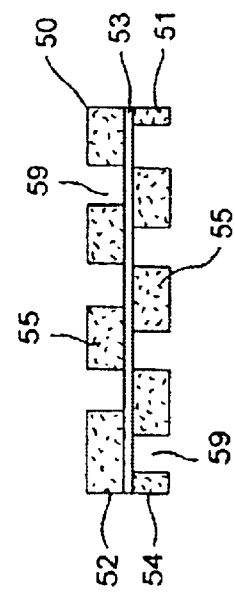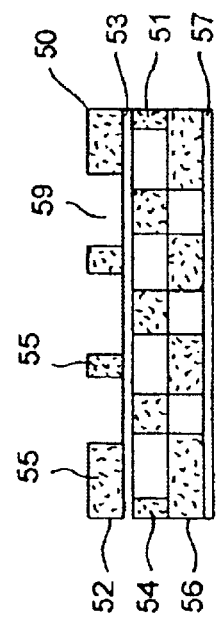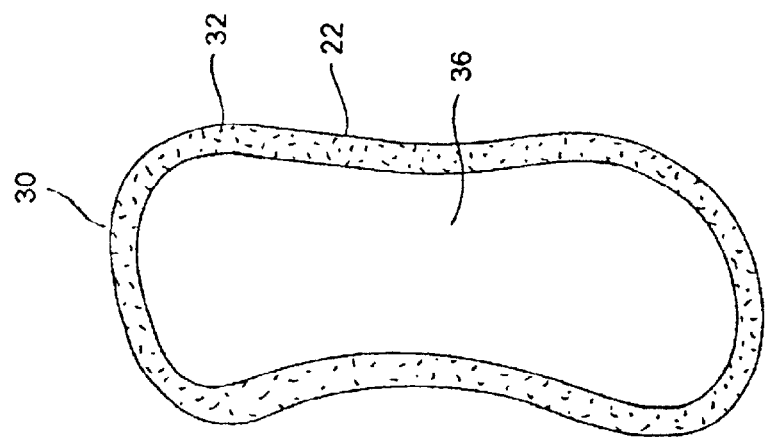

ABSORBENT STRUCTURES WITH SELECTIVELY PLACED FLEXIBLE ABSORBENT BINDER

RELATED APPLICATIONS

This application is a continuation-in-part of U.S. patent application Ser. No. 10/206,883, filed on Jul. 26, 2002, the disclosure of which is incorporated by reference. This application is also a continuation-in-part of U.S. patent application Ser. No. 10/324,478, filed Dec. 20, 2002, the disclosure of which is incorporated by reference.

BACKGROUND OF THE INVENTION

This invention is directed to absorbent structures having a flexible absorbent binder (FAB) composition selectively formed on a substrate for controlled liquid intake, distribution and absorption properties.

Adhesives, or binders, are a necessary element of many absorbent products. While adhesives beneficially hold products together, adhesives may also have a tendency to interfere with the absorbency of fluids in absorbent products. Adhesives are typically hydrophobic and therefore are not conducive to absorbency or liquid transfer functions. Furthermore, most adhesives are non-absorbent and thus serve no liquid retention function.

Hydrophilic adhesives are known, such as adhesives formulated from water-soluble polymers such as poly(vinyl alcohol), poly(vinyl methyl ether), poly(vinyl pyrrolidone), poly(ethylene oxide), or cellulose derivatives such as hydroxypropyl cellulose. Dextrans, starches and vegetable gums have been used to provide hydrophilic adhesives. These materials provide adhesion under dry conditions. However, upon exposure to aqueous fluids, these materials lose bonding capability because they are substantially soluble in aqueous fluids.

A known approach for making hydrophilic adhesives more functional upon exposure to aqueous fluid is to crosslink the water-soluble polymers. As a result of crosslinking, the material becomes swellable, and no longer soluble, in aqueous fluid. However, crosslinked polymers are difficult to apply to substrates or to establish intimate contact with surfaces because the crosslinked polymers are solid materials and have little or no ability to flow. Some of the crosslinked materials are fairly stiff, and inhibit the flexibility of the absorbent product.

What is therefore needed is a hydrophilic binder or coating that has latent crosslinking capability and which can be produced at attractive cost. Such binder or coating could be easily applied, like a water-soluble polymer, since the hydrophilic binder or coating would be capable of flow prior to crosslinking. Latent crosslinking capability would also provide a simple means of crosslinking the polymer after the polymer has established intimate contact with substrates or has formed a desired final shape or form. There is also a need or desire for such a binder which has a high level of flexibility.

Post-application crosslinking techniques are well known. Typical means of inducing the formation of crosslinks include high temperature "curing" or exposure to radiation, such as ultraviolet or gamma radiation. Another known means of post-application crosslinking is moisture-induced crosslinking.

Recent development efforts have provided coating materials for a variety of uses. For example, U.S. Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing compositions.

Anderson et al., in U.S. Pat. No. 5,196,470, reported an alcohol-based, water-soluble binder composition. Because this composition is water-soluble and not cross-linked, it has no absorbency.

Others have reported the production of graft copolymers having silane functional groups that permitted the initiation of cross-linking by exposure to moisture. Prejean (U.S. Pat. No. 5,389,728) describes a melt-processable, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be useful as adhesives and for wire and cable coatings.

Furrer et al., in U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate.

U.S. Pat. No. 4,593,071 to Keough reported moisture cross-linkable ethylene copolymers having pendant silane acryloxy groups. The resultant cross-linked polymers were reported to be especially resistant to moisture and to be useful for extruded coatings around wires and cables. The same group has reported similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136.

U.S. Pat. No. 5,204,404 to Werner reported crosslinkable hydrophobic acrylate ester copolymers including 0.1 to 10% acrylic acid. The resultant cross-linked polymers were reported to be useful for painting and refinishing the exterior of automobiles.

These examples of moisture-induced crosslinking are applied to substantially hydrophobic polymers. Since the cured products of these formulations are reported to be useful for coverings for wire and cable, and for non-conductive coatings for electrical conductors, and for painting and refinishing the exterior of automobiles, it would be expected that they are durable coatings for which properties such as water absorbency would be a disadvantage.

There is a need for a flexible absorbent binder composition which can be formed at selective locations on or in an absorbent structure for controlling liquid intake, distribution and absorbency as well as stiffness and structural integrity of the absorbent structure. There is also a need for absorbent structures having a flexible absorbent binder formed at selected locations, to achieve these objectives.

SUMMARY OF THE INVENTION

The present invention is directed to an absorbent structure having a flexible absorbent binder provided at predetermined selected locations to provide various advantageous properties. The flexible absorbent binder may be provided (e.g., formed) at predetermined selected locations on an absorbent core, another absorbent structure, or a carrier sheet or substrate, to provide controlled liquid intake, distribution, absorption, flexibility, and/or stiffness to the absorbent structure.

The flexible absorbent binder is formed from a precursor absorbent binder composition which is applied to selected locations on the absorbent structure, and then crosslinked to form the flexible absorbent binder. The flexible absorbent binder is an absorbent or superabsorbent polymer which firmly adheres to the selected locations on the absorbent structure because it is crosslinked and formed directly on the structure. The absorbent structure may be an absorbent core of a personal care article, such as a diaper, diaper pant, sanitary napkin, swimwear or adult incontinence garment. Absorbent cores are generally formed of absorbent materials such as cellulose fluff, wood pulp and the like. The absorbent structure may also be a layer of an absorbent article which is otherwise nonabsorbent, to which absorbency is imparted by inclusion of the flexible absorbent binder.

The absorbent binder composition (useful to form the flexible absorbent polymer) includes a hydrophilic polymer which is capable of post-application, moisture-induced crosslinking, is relatively inexpensive to produce, and has a high level of flexibility. The flexible nature of the absorbent binder is useful when the binder is employed in personal care absorbent articles, as well as in other products which must be flexible and/or conformable to the wearer's body.

The absorbent binder composition includes about 15 to about 99.9% by mass of monoethylenically unsaturated polymer units. Suitable monoethylenically unsaturated polymers include without limitation carboxylic acid, sulphonic acid, phosphonic acid, and salts of the foregoing. The absorbent binder composition also includes about 0.1 to about 20% by mass of acrylate or methacrylate ester units that include an alkoxysilane functionality. Upon exposure to water, the alkoxysilane functionality forms a silanol group which condenses to form a crosslinked polymer, which is the flexible absorbent binder.

The absorbent binder composition may also include zero to about 75% by mass of polyolefin glycol and/or polyolefin oxide units. The polyolefin glycol and/or oxide may include an alpha-olefin having about 2 to about 4 carbon atoms, and may include about 30 to about 15,000 olefin glycol and/or oxide units per molecule. The polyolefin glycol and/or oxide may be graft polymerized with the acrylate or methacrylate ester to form a graft copolymer. The polyolefin glycol and/or oxide may be a homopolymer or copolymer. The polyolefin glycol and/or oxide may be a block copolymer including olefin glycol or oxide units having different numbers of carbon atoms, for instance, block copolymers of ethylene oxide and propylene oxide. The polyolefin glycol and/or oxide provides the absorbent binder composition with enhanced flexibility. Thus, the absorbent binder composition has enhanced adhesion in a wet condition, absorbency, and flexibility.

The absorbent binder composition may be used in the manufacture of absorbent products, and therefore may be selectively applied to such substrates as nonwoven webs, woven webs, knitted fabrics, cellulose tissue, plastic film, stranded composites, staple fibers, yarns, elastomer net composites, or any other suitable substrates. Examples of suitable types of plastic film substrates include those made of polypropylene, low density polyethylene, high density polyethylene, linear low density polyethylene, and ultra low density polyethylene. Examples of absorbent articles in which the flexible absorbent binder may be used include diapers, diaper pants, training pants, feminine hygiene products, adult incontinence products, swimwear garments, and the like.

The absorbent binder composition can be prepared using a template polymerization process by which the monoethylenically unsaturated polymer and acrylate or methacrylate ester are polymerized in the presence of a pre-formed template polymer, which can be the polyolefin glycol and/or polyolefin oxide. The polymerization can be carried out by reacting two different monoethylenically unsaturated monomers, one of which contains an alkoxysilane functionality. The polymerization may be induced by heat, radiation, redox chemical reactions, and other techniques. Suitable radiation initiators include without limitation ultraviolet, microwave, and electron beam radiation. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The resulting absorbent binder composition may contain the polyolefin glycol and/or oxide as a separate component, or as part of the copolymer, or a combination of both.

The resulting absorbent binder composition has latent moisture-induced crosslinking capability due to the alkoxysilane functionality. This composition may be selectively applied, in a flowable state, to the substrate. Moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air. The flexible absorbent binder is thus formed at the selected locations on the resulting absorbent structure.

With the foregoing in mind, it is a feature and advantage of the invention to provide an absorbent structure having a flexible absorbent binder formed on a substrate at selected locations, and adhered to the substrate.

Definitions

Within the context of this specification, each term or phrase below will include the following meaning or meanings.

"Binder" includes materials which are capable of attaching themselves to a substrate or are capable of attaching other substances to a substrate.

"Crotch region" is the central one-third of the longitudinal length of an absorbent structure.

"Front region" or "front end region" is the forward one-third of the longitudinal length of the absorbent structure.

"Back region" or "back end region" is the rearward one-third of the longitudinal length of the absorbent structure.

"Feminine hygiene products" include sanitary pads, towels, and napkins, as well as pantiliners, tampons and interlabial feminine hygiene products.

"Fluid" refers to a substance in the form of a liquid or gas at room temperature and atmospheric pressure.

"High density polyethylene (HDPE)" refers to a polyethylene having a density of about 0.95 g/cm$^3$ or greater.

"Knife over roll coating" refers to a process in which a knife is positioned, with a specified gap, above a substrate that is moving beneath the knife on a moving roll. In this manner, the knife spreads a specified thickness of coating material onto the substrate.

"Layer" when used in the singular can have the dual meaning of a single element or a plurality of elements.

"Linear low density polyethylene (LLDPE)" refers to polymers of ethylene and higher alpha-olefin comonomers such as $C_3$–$C_{12}$ comonomers, and combinations thereof, having a density of about 0.900 to about 0.935 g/cm$^3$.

"Low density polyethylene (LDPE)" refers to a polyethylene having a density between about 0.91 and about 0.925 g/cm$^3$.

"Modifying agent" refers to a substance that may be added to a composition such as the flexible absorbent binder described herein, to modify the physical properties of the composition, such as the color or texture of the composition.

"Nonwoven" or "nonwoven web" refers to materials and webs or material having a structure of fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Personal care absorbent article" includes diapers, diaper pants, training pants, swim wear, absorbent underpants, adult incontinence products, feminine hygiene products, and the like.

"Roll printing" or "roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

"Rotary screen printing" or "rotary screen coating" refers to a process that is a combination of roll printing or coating and screen printing or coating.

"Screen printing" or "screen coating" refers to a method of applying a deposited material by forcing the material to be deposited through a screen that may have uniform openings or patterned openings.

"Stranded composites" refer to sheets of material to which strands of an elastomeric material are adhered to create an elastomeric composite.

"Superabsorbent" refers to a water-swellable, water-insoluble organic or inorganic material capable, under the most favorable conditions, of absorbing at least about 10 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. "Absorbent" refers to materials that absorb at least five times their weight of the aqueous solution under the same conditions.

"Unit" or "polymer unit" refers to a monomer or polymer portion of a copolymer molecule or blend component that includes a different molecular structure, compared to another portion of the copolymer or blend.

BRIEF DESCRIPTION OF THE DRAWINGS

FIG. 5 is a top view of an absorbent article, in this case a sanitary napkin, having a dam of flexible absorbent polymer formed around its periphery to prevent leakage of bodily fluid.

FIGS. 6–12 are edge views of absorbent structures which can be used as absorbent cores or intake (surge) layers in absorbent articles. The absorbent structures are formed using various staggered arrangements of flexible absorbent polymer.

DETAILED DESCRIPTION OF THE PRESENTLY PREFERRED EMBODIMENTS

Disposable absorbent articles such as, for example, many of the feminine care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, the body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

Figure 1:
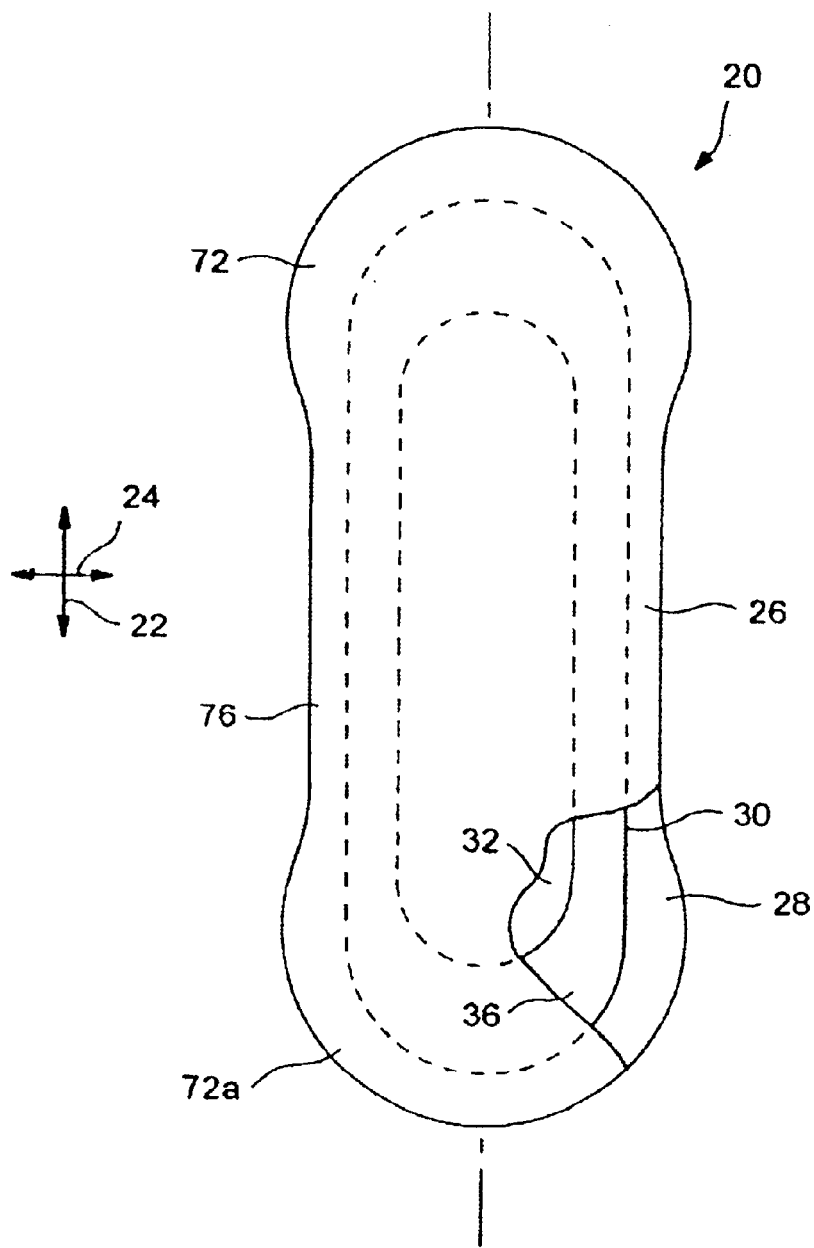
FIG. 1 is a partially cut away top view of an absorbent article, in this case a sanitary napkin.
Figure 1A:
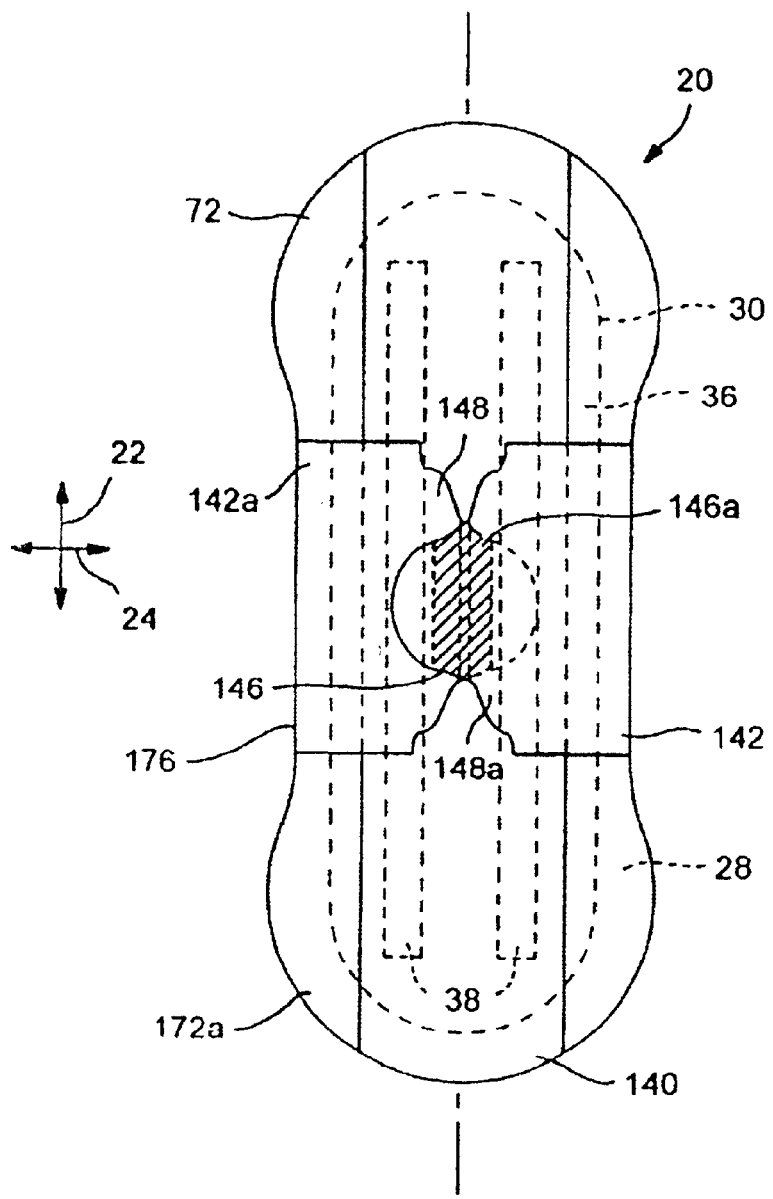
FIG. 1A is a partially cut away bottom view of the absorbent article of FIG. 1.
Figure 1B:
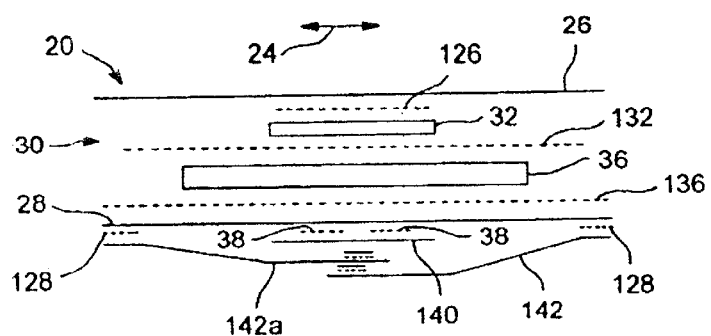
FIG. 1B is a sectional view of the absorbent article of FIG. 1, taken along a lateral direction 24 through the longitudinal center of the article.
Figure 1C:
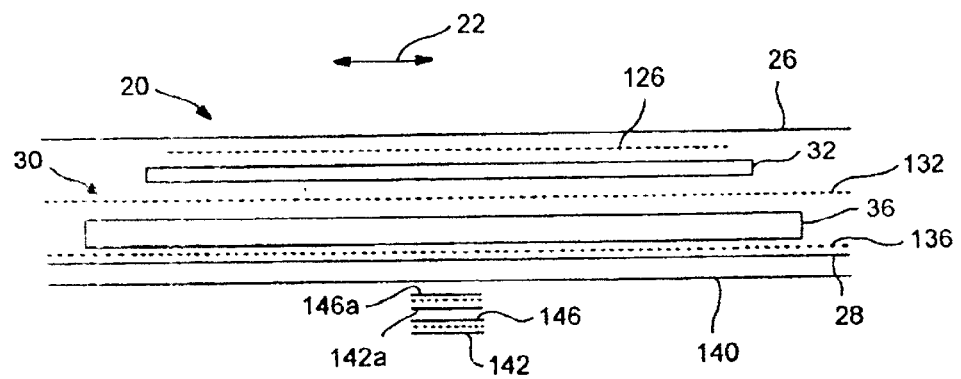
FIG. 1C is a sectional view of the absorbent article of FIG. 1, taken along a longitudinal direction 22 through the lateral center of the article.

FIGS. 1 through 1C illustrate an example of a suitable article, such as the representatively shown feminine care article. Referring to FIG. 1, the feminine care article can, for example, be a feminine care pad or napkin 20, and the article can have a lengthwise longitudinal direction 22, a transverse, laterally extending cross-direction 24, first and second longitudinally opposed end portions 172 and 172a, and an intermediate portion 176 located between the end portions. As representatively shown, the longitudinal dimension of the article is relatively larger than the lateral dimension of the article. The article 20 can include a topsheet or cover 26, a baffle 28, and an absorbent structure 30 positioned between the cover and baffle. The absorbent structure 30 can at least include an intake layer 32 and a shaping or absorbent layer 36.

Referring to FIG. 1, the absorbent article 20, in this case a sanitary napkin, may embody one or more of the absorbent structures of the invention. In the lower section of FIG. 1 layers, respectively, of the article 20 of the invention have in part been cut out to show the layers below. The lowermost layer (outer cover or baffle) of the article 20 is formed by a liquid-impermeable layer 28. The liquid-impermeable layer 28 can be made of a polypropylene film, for instance. The liquid-impermeable layer 28 serves as so-called garment-protecting layer which prevents liquid which has penetrated into the absorbent article and which is retained therein from escaping downwards from the absorbent body. This prevents the wearer's undergarment from being stained. The liquid-impermeable layer 28, which is referred to synonymously as an outer cover or baffle, can be breathable to water vapor.

Referring to FIG. 1A, the absorbent article 20 also includes two laterally extending, inward folding wings 142 and 142a, hook fastening materials 146 and 146a attached to inner surfaces of end regions of the wings, respectively, and loop fastening materials 148 and 148a attached to or forming part of outer surfaces of the user's end regions of the wings. When the wings 142 and 142a are folded inward as shown, over a wearer's garment, the hook and loop fastening regions overlap and engage each other to secure the absorbent article 20 in place. Adhesive bands 38 can be used to secure the baffle 28 to a peelable release layer 140. When the release layer 140 is removed (peeled away), the bands 38 of adhesive provide additional securement of the absorbent article 20 to an inner surface of the wearer's garment.

FIGS. 1B and 1C illustrate exploded sectional views of the absorbent article 20, shown in the lateral direction 124 (FIG. 1B) and in the longitudinal direction 122 (FIG. 1C). As illustrated, the topsheet 26 and intake layer 32 are adhered together by a first adhesive layer 126. The intake layer 32 and absorbent layer 36 are adhered together by a second adhesive layer 132. The absorbent layer 36 and baffle 28 are adhered together by a third adhesive layer 136. The wings 142 and 142a may be bound at manufacturer's ends thereof to the baffle 28 by adhesive bands 128.

Additional absorbent structures, namely feminine care pad designs, are described in U.S. patent application Ser. No. 10/379,942, filed on Mar. 4, 2003, entitled "Perimeter Embossing In An Absorbent Article," and in U.S. patent application Ser. No. 10/392,116, filed on Mar. 19, 2003, entitled "Multilayer Absorbent Article." These documents are incorporated by reference.

Figure 4:
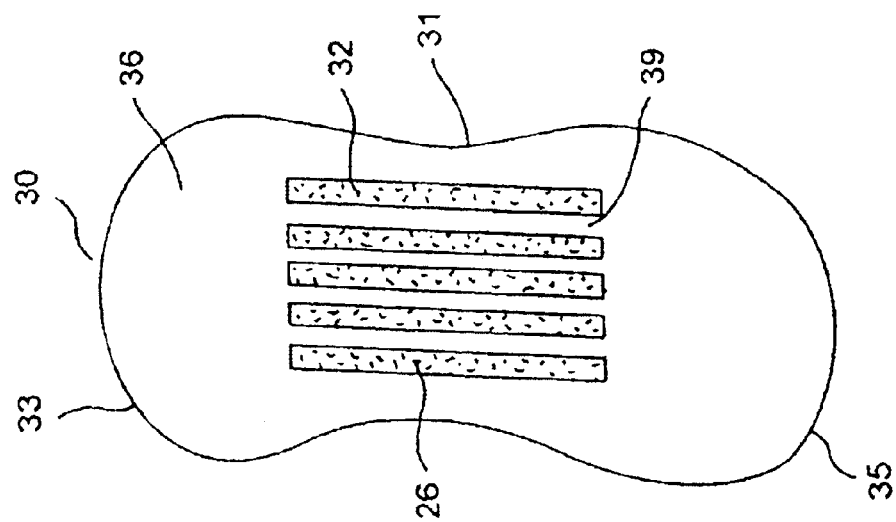
FIGS. 2, 3 and 4 are top views of absorbent structures, in this case absorbent cores useful in the sanitary napkin of FIGS. 1–1C. The absorbent cores include flexible absorbent polymer formed in selected locations for controlled fluid intake, distribution and absorption.
Figure 3:
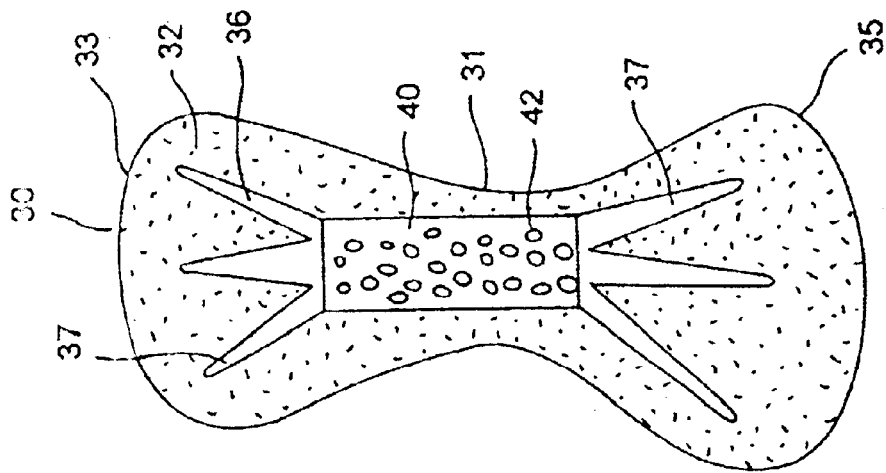
Figure 2:
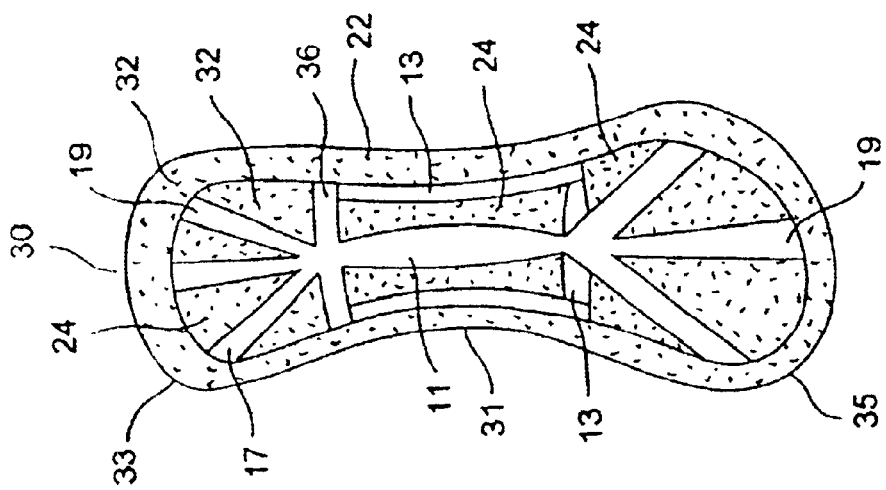

FIGS. 2–4 illustrate various embodiments of absorbent structure 30 in which a flexible absorbent binder, formed at selected locations designated by shaded regions, serves as or replaces the intake layer 32 of the absorbent structure 30. The flexible absorbent binder layer 32 may be formed at selected locations on the absorbent layer 36, which may have a conventional absorbent construction as shown. Alternatively, in some embodiments, the absorbent layer 36 may be omitted, and the flexible absorbent binder layer 32 may be selectively formed directly on the liquid impermeable outer cover of the absorbent article and may provide suitable absorbent capacity. In each of FIGS. 2–4, the flexible absorbent binder layer 32 is formed at selected locations to provide channels therebetween which facilitate liquid intake, distribution and absorption by the absorbent core 15 or into the flexible absorbent binder layer 32.

Referring to FIG. 2, the flexible absorbent binder layer 32 forms a dam 22 around the outer periphery of absorbent structure 30, to facilitate peripheral absorption and alleviate leakage of fluid from around the periphery. Additionally, the flexible absorbent binder occupies a plurality of locations 24 inward from the dam 22. The inward locations 24 of flexible absorbent binder, and the dam 22, define a network 17 of channels which are devoid of flexible absorbent binder, and which facilitate liquid intake and distribution. The channel network 17 includes a relatively wide central channel 11 longitudinally bisecting a central region 31 of the absorbent structure 30, and four interconnecting narrower channels 13 surrounding the central region 31. The channel network 17 also includes a plurality of radially projecting channels 19 in a front region 33 and a back region 35 of the absorbent structure 30. The channels 19 become gradually wider as they approach the dam 22.

FIG. 3 illustrates another embodiment of absorbent structure 30 in which the flexible absorbent binder layer 32 covers a substantial portion of the front and back regions 33 and 35, and the peripheral portions of the central region 31. Openings in the flexible absorbent binder layer 32 define channels 37 in the front and back regions 33 and 35. Channels 37 are wider toward the central region 31, and become progressively narrower away from the central region, with each channel 37 terminating at a point in the front or back region 33 or 35. The flexible absorbent binder layer 32 also defines a rectangular area 40 in the central region 31. The channels 37 and the small openings 42 of the rectangular area 40 may permit liquid entering the absorbent structure to quickly pass directly to the lower absorbent layer 36 of the absorbent structure 30, or to the impermeable baffle 28 if a lower storage layer is not used. The absorbent layer 36 or impermeable baffle 28 may laterally distribute some of the liquid and pass it up to the flexible absorbent binder layer 32.

In the absorbent structure 30 of FIG. 4, the flexible absorbent binder layer 20 includes only a plurality of elongated rectangles 26 extending longitudinally in and through the central region 31. The lower absorbent layer 36 is exposed substantially throughout the front and back regions 33 and 35, near the peripheral edges of the central region 31, and in channels 39 formed between the rectangles 26 in the central region. In the absorbent core of FIG. 4, much of the liquid would be absorbed by the rectangles 26 of flexible absorbent binder, causing swelling and widening of the rectangles 26.

In each of the embodiments of FIGS. 2–5, the channels defined by voids in the flexible absorbent binder layer 32 serve the dual purposes of a) facilitating liquid distribution, and b) permitting expansion of the flexible absorbent binder when it becomes wet. By providing room for the flexible absorbent binder to expand, gel blocking is alleviated. In various embodiments, the lower absorbent layer 36 may be composed entirely of absorbent fibers such as wood pulp or cellulose fluff, or may include additional particles or fibers of superabsorbent polymer for enhanced absorption. In some instances, the flexible absorbent binder layer may be present without a lower storage layer. FIG. 5 illustrates an embodiment of absorbent structure 30 in which the flexible absorbent binder layer 20 is employed only as a peripheral dam 22. In this embodiment, it may be advantageous to mix superabsorbent particles or fibers with the cellulose fluff in lower storage layer 14, for enhanced absorption.

Superabsorbent particles or fibers can also be mixed with and incorporated into the flexible absorbent binder or bound to its surface. A modifying agent, such as a menses modifying agent, can also be combined with the flexible absorbent binder. These additives improve the retention functionality of the structure and provide desired product absorbent capacity to reduce leakage. The increased functionality can diminish the need for a lower absorbent layer 36.

FIGS. 6–12 are edge views of absorbent structures which incorporate the flexible absorbent binder in a variety of layered configurations to enhance fluid intake and absorption and alleviate gel blocking. In each instance, the flexible absorbent binder may be applied in rectangles or stripes, for instance, as in FIG. 4. However, unlike FIG. 4, the flexible absorbent binder in FIGS. 6–12 is applied in two or more layers. Also, the absorbent structures shown are not necessarily limited to absorbent cores, but may be used as surge layers, cover material layers, other intake layers, or lower storage layers in absorbent articles. The stripes, rectangles or the like of flexible absorbent binder are shown in edge view in FIGS. 6–12.

Referring to FIG. 6, the absorbent structure 50 includes three layers 52, 54 and 56 of flexible absorbent binder. The layers 52 and 54 are formed on first and second sides of a liquid pervious layer which may be a nonwoven material or an intake layer, for instance, a bonded carded web. The layer 56 is formed on a support layer 57 which, depending on the position of structure 50 in an absorbent article, may be another liquid permeable (e.g., intake) layer or a liquid impermeable (e.g., outer cover) layer.

Each of the flexible absorbent binder layers 52, 54 and 56 includes a plurality of rectangles 55 of flexible absorbent binder, with spaces 59 between the rectangles. The rectangles 55 are spaced apart within each layer and are offset (staggered) in the adjacent layers, so that a) the rectangles 55 of flexible absorbent binder may expand when wet, without blocking fluid flow, and b) fluid may flow between the rectangles 55 from one of the layers 52, 54, 56 to the next. Both of these features facilitate fluid flow and absorption, and alleviate gel blocking. The fluid can quickly migrate to the support layer 57 for absorption or distribution along the length of the product. The upper layers 52 and 54 are available for additional retention capacity with increased fluid loadings. The rectangles 55 may be replaced with other shapes of flexible absorbent binder, so long as the flexible absorbent binder in each layer is applied at a plurality of locations, desirably in stripes, with spaces between the locations. In the embodiment shown, the rectangles are configured to provide a vertically continuous dam 51 of flexible absorbent binder at the peripheral edges of the absorbent structure.

The absorbent structure 50 of FIG. 7 resembles the one shown in FIG. 6, except that there are only two layers 52 and 54 of flexible absorbent binder, formed on opposing sides of a liquid permeable layer 53. The stripes or rectangles 55 of flexible absorbent binder are spaced apart and staggered in much the same fashion as in the upper layers 52, 54 in FIG. 6.

The absorbent structure 50 of FIG. 8 resembles the one shown in FIG. 6 except that the stripes or rectangles 55 of flexible absorbent binder are relatively narrower in the two upper layers 52, 54. Some of the rectangles 55 in the upper layer 52 are particularly narrow, with wide spaces 59 between them. The rectangles 55 in the middle layer 54 are relatively narrow in the absorbent structure of FIG. 8, compared to the absorbent structure of FIG. 6. The effect of using narrower stripes or rectangles 55 of flexible absorbent binder is that the absorbent structure 50 of FIG. 8 is more open, and facilitates more rapid fluid flow between the layers.

Figure 9:
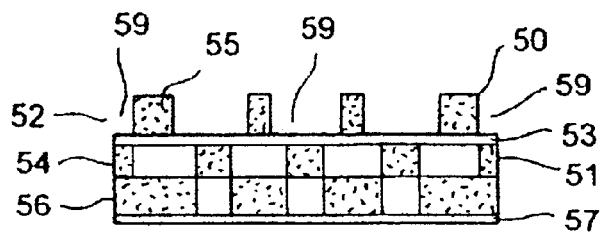

The absorbent structure 50 of FIG. 9 is very similar to the one shown in FIG. 8. The difference is that, in FIG. 9, there is no continuous peripheral dam 51 formed of flexible absorbent binder rectangles 55 in all three layers. The dam 51 is formed only in the middle and lower layers 54 and 56 of flexible absorbent polymer, and not in the upper layer 52.

Figure 10:
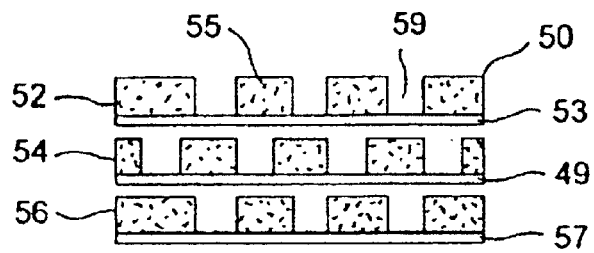

In the absorbent structure 50 of FIG. 10, each of the layers 52, 54 and 56 of flexible absorbent binder is formed on a separate substrate layer. The substrate layer 53 supporting layer 54 of flexible absorbent binder, and the substrate layer 49 supporting layer 54 of flexible absorbent binder, are each liquid permeable intake layers, for instance, spunbond webs. The substrate layer 57 supporting layer 56 of flexible absorbent binder may be liquid-permeable layer or liquid impermeable, depending on where the absorbent structure 50 is positioned in an absorbent article. If the absorbent structure 50 is positioned as a cover layer facing a bodyside liner, or as a surge layer, or both, then the lower support layer 57 may be liquid-permeable, and may be positioned above an absorbent core. If the absorbent structure 50 is used essentially as an absorbent core, then the lower support layer 57 may be liquid-impermeable, for instance, an outer cover.

By having each of the flexible absorbent binder layers 52, 54 and 56 independently supported as shown in FIG. 10, they may be positioned so that they can move and shift relative to each other during use, without binding the flexible absorbent binder layers to each other. This arrangement further facilitates passage of liquid between the layers. Liquid transport and distribution are further enhanced, and gel blocking is further reduced. The offset flexible absorbent binder stripes in the absorbent structures described in FIGS. 6–10 also allow the absorbent core to form an inverted "V" shape or W-fold geometry under lateral compression between the wearer's legs. An inverted "V" shape or W-fold geometry can also provide positive shaping of the layers for more comfortable fit, less bunching, and optimal contact of the flexible absorbent binder with the fluid source. Stripes of flexible absorbent binder can be configured for optimal comfort and fit as well as fluid distribution and storage.

Figure 11:
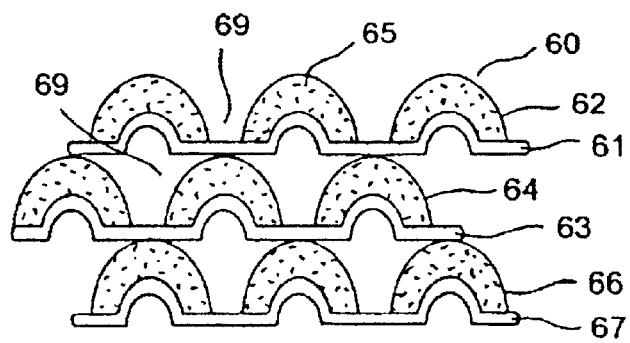

FIG. 11 illustrates an absorbent article 60 in which the flexible absorbent binder layers 62, 64 and 66 are composed of spaced apart, semi-cylindrical or horseshoe-shaped members 65 of flexible absorbent binder. The members 65 in each layer are formed, respectively, on substrates 61, 63 and 67 which have a three-dimensional topography. Examples of three-dimensional substrates 61, 63 and 67 which are liquid permeable include creped nonwoven webs (e.g., spunbond webs), creped apertured thermoplastic films, and nonwoven webs and apertured films which have been embossed or otherwise molded to have a three-dimensional topography. The semi-cylindrical configuration of flexible absorbent binder members 65 results in relatively large open channels 69 between the adjacent layers of flexible absorbent polymer, and between the individual members 65 of a given layer.

Figure 12:
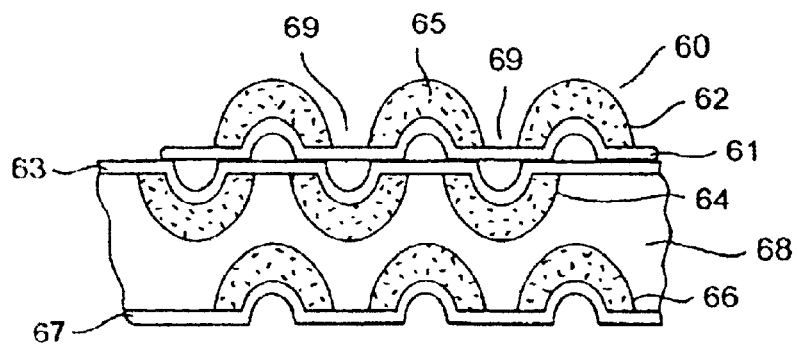

The absorbent article 60 of FIG. 12 also includes three layers 62, 64 and 66 of semi-cylindrical flexible absorbent binder members 65, each formed on a separate three-dimensional substrate 61, 63 or 67. In the embodiment of FIG. 12, the layers 64 and 66 are inverted relative to each other and the space between them is filled with a layer 68 of conventional absorbent material, such as a layer including wood pulp or cellulose fluff. In this embodiment, the absorbent layers 64, 66 and 68 may together perform a primary storage function in an absorbent core, whereas the absorbent layer 62 may perform liquid receiving and distribution functions, and a secondary storage function.

Figure 13:
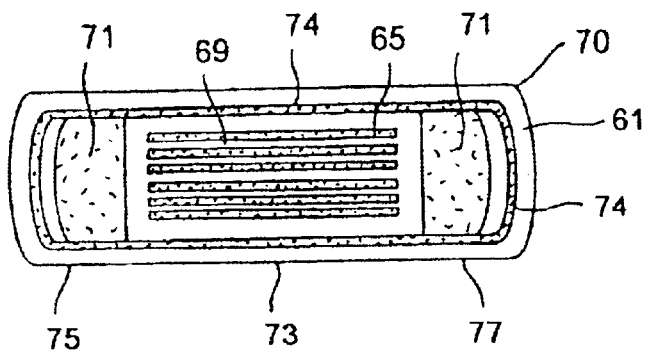
FIG. 13 is a top view of an absorbent structure in which flexible absorbent material is configured to form an interior channel system and a peripheral dam system.

FIG. 13 is a top view of an absorbent structure 70 which can include the three-dimensional flexible absorbent binder topography illustrated in any of FIGS. 6–12. Absorbent structure 70 includes an illustrated substrate layer 61, which is a generally liquid permeable three-dimensional substrate as described above. Semi-cylindrical flexible absorbent binder members 65 are oriented in the longitudinal direction of the absorbent structure in the central region 73, and are separated by channels 69. A large storage area 71 of flexible absorbent binder is provided in each end region 75 and 77 of the absorbent structure 70. A much narrower peripheral dam 74 is provided near the perimeter over the entire circumference of the absorbent structure 70. The absorbent structure 70 may be used in an absorbent article, for instance a feminine care pad, with the channels 69 serving to move amounts of the received fluid into both end regions for storage in the large storage areas 71. The peripheral dam 74 prevents fluid leakage from the sides and ends. The substrate 61 is typically liquid permeable, for instance, an absorbent layer of cellulose fluff. However, the substrate 61 may also be a liquid impermeable outer cover if it is desired to simplify the absorbent structure 70 and minimize its thickness.

Figures 14, 15, 16:
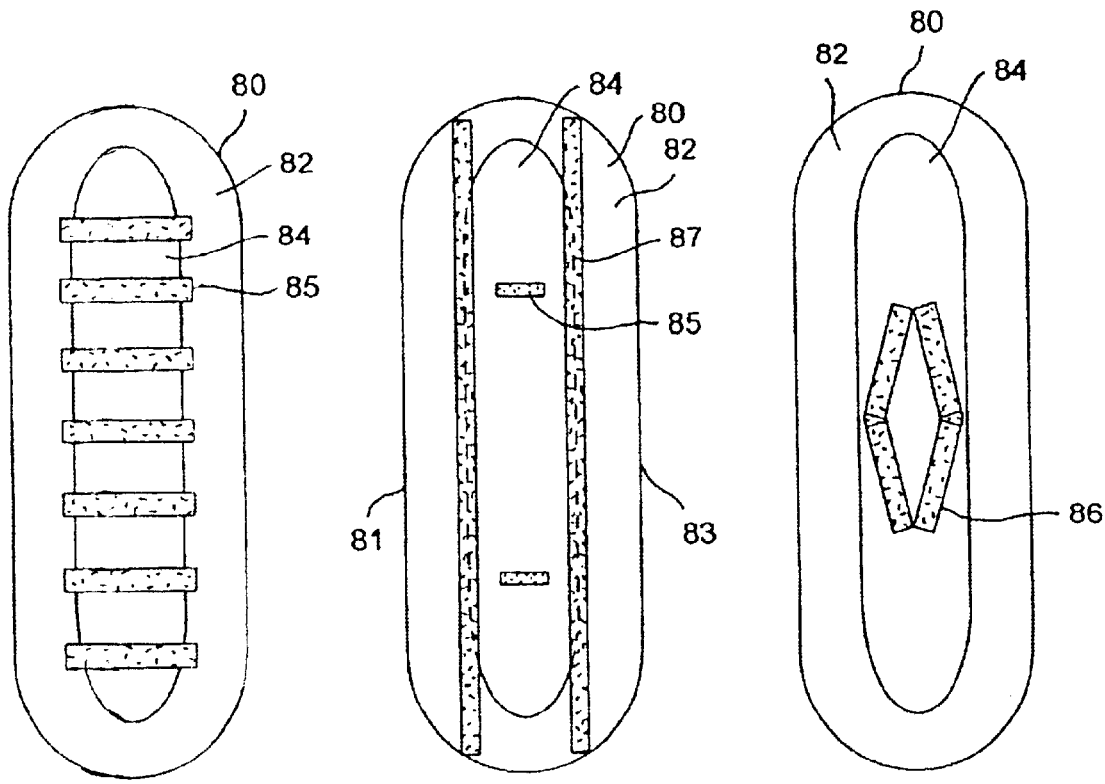
FIGS. 14–16 are top views of absorbent structures, for instance absorbent cores, on which flexible absorbent material is disposed in patterns resembling braces to control the resiliency and folding properties of the absorbent structures.

FIGS. 14–17 illustrate absorbent articles in which the flexible absorbent binder is applied at selected locations to control the stiffness, resiliency and folding properties of the article when under lateral compression from the user's legs. Referring to FIG. 14, an absorbent article 80, which can be a sanitary napkin, includes a wider chassis portion 82 including a bodyside liner and outer cover, for instance, and a narrower absorbent core 84. This absorbent article can be rectangular or shaped. A plurality of stripes 85 of flexible absorbent binder are positioned parallel to each other, overlying the core 84 in the lateral direction. The stripes 85 of flexible absorbent binder may be formed directly on the absorbent core 84, or may be formed on a liquid receiving layer above the core. The stripes 85 of flexible absorbent binder may also be formed on the liquid-impermeable outer cover (baffle) 28. In addition to providing enhanced absorbency, the stripes 85 of flexible absorbent binder act as braces which discourage lateral folding and bunching of the absorbent core, both during storage and during use on a wearer. The braces promote raising of the central region of the article into an inverted "V" shape to provide more intimate contact at points of fluid entry, resulting in less leakage and a more comfortable fit. This pattern can be combined with other patterns, such as described in FIGS. 2–13

FIG. 15 illustrates, in plan view, an absorbent article similar to the one shown in FIG. 14 except for differences in the flexible absorbent binder stripes. In the absorbent article of FIG. 15, the stripes 85 of flexible absorbent binder are formed laterally in or over the absorbent core 84. The stripes 85 are laterally centered on or over the absorbent core, but do not have sufficient length in the lateral direction to completely traverse the absorbent core. Two longitudinal stripes 87 of flexible absorbent binder are formed along the lateral edges of the absorbent core, and extend the length of the absorbent article 80. The longitudinal stripes 87 can be formed on the impermeable outer cover, or underneath, in or on the absorbent core 84.

Figure 17:
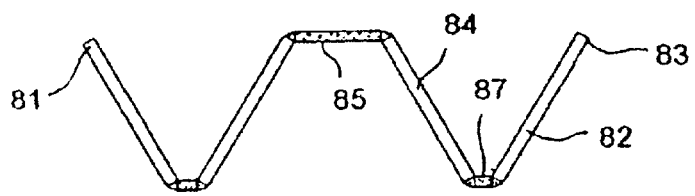
FIG. 17 is an edge view of the absorbent structure of FIG. 15, showing how the flexible absorbent polymer may influence the folding pattern.

In addition to providing controlled absorption properties and fit, the distribution of flexible absorbent binder shown in FIG. 15 permits the article 80 to have a W-shaped lateral folding shown in edge view in FIG. 17. By applying an inward force at both lateral edges 81 and 83 of the absorbent article similar to the compressive forces of the user's legs, this W-shaped folding can be achieved. If the flexible absorbent binder were not selectively positioned as shown in FIG. 15, or in another helpful configuration, the W-shaped folding would be difficult to achieve. The W-shaped folding is useful to promote positive shaping of the layers for more comfortable fit, less bunching, and optimal contact of the flexible absorbent binder with the fluid source, leading to less leakage. This pattern can be combined with other patterns, such as described in FIGS. 2–13.

FIG. 16 illustrates, in plan view, another embodiment of the absorbent article. In the embodiment of FIG. 16, four stripes 86 of flexible absorbent binder are formed in a diamond configuration in the crotch region of the absorbent article. The diamond-shaped arrangement of flexible absorbent binder provides both elevation ("lift") and increased absorbent capacity to the crotch region during wear. The diamond-shaped arrangement can be formed on the impermeable outer cover 28, or underneath, in or on the absorbent core 84. This arrangement also promotes W-shaped folding of the absorbent article during wear. This pattern can be combined with other patterns, such as described in FIGS. 2–13.

Superabsorbent can play a role in each of the described patterns of flexible absorbent binder in FIGS. 2–16. Retention can be increased and improved with the binding of superabsorbent onto the flexible absorbent binder. Additionally, modification of the menses with the use of menses modifying agents also bound to the flexible absorbent binder can also improve fluid movement and retention within the flexible absorbent binder.

The absorbent binder composition (used to form the flexible absorbent binder) includes about 15 to about 99.9% by mass of monoethylenically unsaturated polymer units, suitably about 25 to about 90% by mass, particularly about 30-80% by mass, or about 50 to about 70% by mass. Suitable monoethylenically unsaturated polymer units include without limitation monoethylenically unsaturated carboxylic acid units and salts thereof, monoethylenically unsaturated sulphonic acid units and salts thereof, and monoethylenically unsaturated phosphonic acid units and salts thereof. Suitable monoethylenically unsaturated monomers that can be used to form the monoethylenically unsaturated polymer units include without limitation:

a) Carboxyl group-containing monomers including monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid;

b) Carboxylic acid anhydride group-containing monomers, including monoethylenically unsaturated polycarboxylic acid anhydrides (such as maleic anhydride);

c) Carboxylic acid salt group-containing monomers including water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate), sodium maleate, methylamine maleate;

d) Sulfonic acid group-containing monomers, including aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

e) Sulfonic acid salt group-containing monomers, including alkali metal salts, ammonium salts, amine salts of sulfonic acid group containing monomers as mentioned above; and/or f) Amide group-containing monomers, including vinylformamide, (meth)acrylamide, N-alkyl (meth) acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth)acrylamide], 3-acrylamidopropyl trimethyl ammonium chloride, vinyl lactams (such as N-vinylpyrrolidone).

The absorbent binder composition also includes about 0.1 to about 20% by mass of polyacrylate ester units, such as acrylate and/or methacrylate ester units, that include an alkoxysilane functionality. The acrylate and/or methacrylate ester units are copolymerized with the monoethylenically unsaturated monomer units. In particular, the absorbent binder composition may include about 0.5 to about 15% by mass of the acrylate and/or methacrylate ester units, for instance about 1.0 to about 10% by mass, for instance about 1.5 to about 5.5% by mass.

The alkoxysilane functionality is a functional group or moiety that reacts with water to form a silanol group. One suitable alkoxysilane group is a trialkoxy silane group having the following structure:

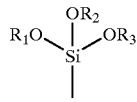

wherein $R_1$, $R_2$ and $R_3$ are alkyl groups independently having from 1 to 6 carbon atoms.

The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Suitable ethylenically unsaturated monomers include acrylates and methacrylates. A particularly ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects are effective monomers for copolymerization in accordance with the present invention.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to, tetramethoxysilane.

The absorbent binder composition may also include zero to about 75% by mass polyolefin glycol and/or polyolefin oxide units, suitably about 5 to about 75% by mass, particularly about 10 to about 60% by mass, particularly about 20 to about 50% by mass, particularly about 30 to about 40% by mass. The polyolefin glycol or oxide may be a glycol or oxide of an olefin polymer having about 2 to about 4 carbon atoms. Polyethylene glycol, polyethylene oxide, polypropylene glycol and polypropylene oxide are examples of suitable polymer units. The polyolefin glycol and/or polyolefin oxide may include on average about 30 to about 15,000 glycol and/or oxide units per molecule. The weight average molecular weight of polyolefin glycol units may range from about 200 to about 8000. When polyolefin oxide units are employed, they may have a weight average molecular weight of about 100,000 to about 600,000.

Polyolefin glycols and polyolefin oxides are commercially available, and are common. To prepare the absorbent binder composition, a pre-formed polyolefin glycol and/or oxide may be dissolved or dispersed in a reaction vessel which includes an aqueous solvent or carrier, an organic solvent or carrier such as ethanol, or a miscible combination of aqueous and organic solvent or carrier. The monomers used to form the monoethylenically unsaturated polymer units and the polyacrylate ester units are added to the solution and polymerized using a template polymerization process in which the polyolefin glycol or oxide serves as a template polymer. Before initiation, the polar groups of the monomers, for instance the acid groups of acrylic acid, are attracted to the polyolefin glycol and/or polyolefin oxide through hydrogen bonding. The steric alignment of the monomers, with the polyolefin glycol and/or oxide serving as backbone, aids in the polymerization and typically increases the chain length of the polymerizing unit. During the polymerization, radical polymerizing chains may become attached to the template polymer, resulting in grafting of polyolefin glycol and/or oxide to the copolymer being formed. However, this graft polymerization need not occur.

The resulting absorbent binder composition includes the polyolefin glycol and/or oxide attached to, and/or blended with, the copolymer of the monoethylenically unsaturated polymer units and the acrylate or methacrylate ester units that include the alkoxysilane functionality.

The polymerization may be initiated using a variety of methods, including without limitation thermal energy, ultraviolet light, and redox chemical reactions. A solution of the above ingredients may be added to an initiator solution at a temperature suitable for generating free radicals, for instance about 50 to about 90° C. An initiator may be prepared by dissolving an initiator in an organic or aqueous solvent. A suitable class of initiators are organic peroxides and azo compounds, with benzoyl peroxide and azobisisobutylnitrile (ABN) as examples.

Compounds containing an O—O, S—S, or N=N bond may be used as thermal initiators. Compounds containing O—O bonds; i.e., peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis (cyclohexanecarbonitrile) may be used as the initiator.

Alternatively, redox initiation can be used for the polymerization. This method incorporates a first monomer solution that includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g., a redox reaction, thereby initiating a polymerization reaction to form a binder composition including a monoethylenically unsaturated monomer and an ethylenically unsaturated monomer that has post-application, moisture-induced crosslinking capability.

In one embodiment, the monoethylenically unsaturated polymer unit is a cationic polymer. The cationic polymer is advantageous because it provides a) inherent antimicrobial properties, b) enhanced attraction and retention into cellulose fibers in a suspension, and c) enhanced attraction to superabsorbent particles which are negatively charged. Suitable cationic polymers include those prepared by copolymerizing a monomer 1) selected from a) acryloyloxyethyl-trialkyl-substituted ammonium salts, b) acryloyloxypropyl-trialkyl-substituted ammonium salts, c) acrylamidoethyl-trialkyl-substituted ammonium salts, and d) acrylamidopropyl-trialkyl-substituted ammonium salts, with a monomer 2) selected from a) methacryl esters which contain an alkoxysilane group capable of moisture-induced crosslinking and b) acryl esters which contain an alkoxysilane group capable of moisture-induced crosslinking. Other monomers may also be present, for instance, an acrylic acid or acrylamide. The polymerization is conducted in the presence of a polyolefin glycol and/or polyolefin oxide as described above, suitably a polyethylene glycol. The cationic monoethylenically unsaturated monomer unit and the polyolefin glycol are present in the amounts described above.

The cationic monoethylenically unsaturated polymer may be prepared by a redox initiation process, according to the following reaction. The cationic copolymer is then coated and dried onto a substrate to form the crosslinked absorbent coating.

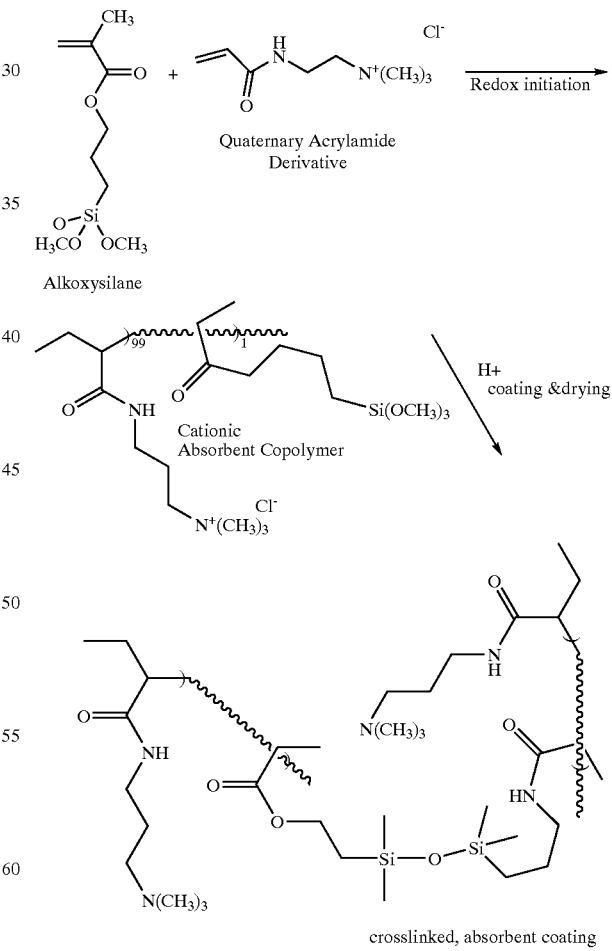

In one embodiment, the absorbent binder composition is made by combining a first aqueous monomer solution including a reducing polymerization initiator with a second aqueous monomer solution including an oxidizing polymerization initiator, wherein the initiators react to form a binder composition. The first aqueous monomer solution further includes a monoethylenically unsaturated monomer and an ethylenically unsaturated monomer that contains an alkoxysilane functionality. The second aqueous monomer solution includes a monoethylenically unsaturated monomer. One or both solutions may include the polyolefin glycol and/or polyolefin oxide template polymer. Suitably, the binder composition is formed in about 100 minutes or less, or about 60 minutes or less, desirably in about 30 minutes or less, or about 15 minutes or less, or about 10 minutes or less.

The pH of the first and/or second aqueous monomer solution is adjusted to about 4.5 to about 8, suitably about 5.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 4.5 to about 8, suitably about 5.5 to about 7.0.

The amounts of the polymerization ingredients added to the first and second aqueous solutions are selected so as to produce the absorbent binder composition having the composition described above. In one embodiment, a surfactant may be added to the first and/or second aqueous monomer solution to disperse the ethylenically unsaturated monomer.

The first aqueous monomer solution further includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g. a redox reaction, thereby initiating a polymerization reaction to form a binder composition including a monoethylenically unsaturated monomer and an ethylenically unsaturated monomer that has post-application, moisture-induced crosslinking capability.

To form the flexible absorbent binder, the absorbent binder composition may be applied to the substrate at selected locations and dried. Once the absorbent binder composition is applied to the substrate, crosslinking can be moisture-induced by hydrolysis and condensation of alkoxysilanes. For example, crosslinking of the absorbent binder composition can be induced by concentrating the binder composition on the substrate through the removal of the water to promote condensation of silanols generated by hydrolysis of alkoxysilanes. Typically, crosslinking begins at a solution concentration of about 30 percent or greater by weight binder composition. Furthermore, if the substrate material has hydroxyl group functionality on its surface, then the silanols within the absorbent binder composition may react with the hydroxyl groups to form a covalent bond between the binder and the hydroxyl-containing surface. Non-limiting examples of substrates with hydroxyl surface functionality include cellulose substrates, as used in an absorbent core.

As explained above, the substrate may be any layer in an absorbent article, including an absorbent core layer, a compensation (surge) layer, a bodyside cover layer or liner, or an outer cover layer. The substrate may be liquid permeable or impermeable, and may be a cellulose layer, a thermoplastic spunbond or meltblown layer, another nonwoven layer, or a thermoplastic film. Personal care absorbent articles include without limitation diapers, training pants, feminine hygiene articles, adult incontinence garments, swimwear garments, medical absorbent articles and the like. The absorbent article may also be a medical absorbent article, such as a garment, gown, apron, pad, towel, wipe, bandage, wound dressing or the like. The binder composition may be selectively applied to the substrate using any application process suitable for forming flexible absorbent binder in a spaced apart, patterned coverage. Printing applications are suitable application techniques, including gravure printing, screen, and jet printing. The binder composition may also be selectively applied to the substrate using a selective spraying or dripping apparatus.

In another embodiment, the absorbent binder composition may be prepared using a continuous process wherein the polymerization and/or neutralization reaction is carried out in a suitable reactor that conveys the resulting binder composition, upon completion of the polymerization reaction, directly to an apparatus for applying the absorbent binder composition onto the substrate. Such a continuous process may be desirable where conditions, such as high heat, may cause premature crosslinking of the binder composition that would hinder application of the absorbent binder composition onto the substrate.

One advantage of the absorbent binder composition of the invention is that it provides a water-soluble ionic polymer capable of sufficient spontaneous crosslinking within about 10 minutes, at a temperature not more than about 120° C., to form a flexible absorbent polymer having an absorbent capacity of at least one gram of fluid per gram of absorbent binder composition, suitably at least three grams of fluid per gram of absorbent binder composition, using the centrifuge retention capacity test described herein. The term "spontaneous" crosslinking refers to crosslinking which occurs without radiation, catalysis, or any other inducement other than the specified temperature of not more than about 120° C., suitably not more than about 100° C. Eliminating the need for radiative crosslinking provides a significant processing advantage. The crosslinking at temperatures not more than about 120° C., suitably not more than about 100° C., permits the absorbent binder composition to be applied to a substrate such as an absorbent article, and then crosslinked without degrading or damaging the substrate. Significant crosslinking occurs within about 10 minutes, suitably within about 8 minutes, particularly within about 6 minutes to provide an efficient, commercially feasible, cost-effective crosslinking process. The crosslinking continues until the desired level of absorption is achieved. The ionic polymer may bear a positive charge, a negative charge, or a combination of both, and should have an ionic unit content of about 15 mole percent or greater. The ionic polymer may include a variety of monomer units described above, and suitably contains a carboxyl group-containing unit or a quaternary ammonium-containing unit.

Test Method for Determining Absorbent Capacity

As used herein, the Centrifuge Retention Capacity (CRC) is a measure of the absorbent capacity of the superabsorbent material retained after being subjected to centrifugation under controlled conditions. The CRC can be measured by placing a sample of the material to be tested into a water-permeable bag which will contain the sample while allowing the test solution (0.9 percent NaCl solution) to be freely absorbed by the sample. A heat-sealable tea bag material (available from Dexter Nonwovens of Windsor Locks, Conn., U.S.A., as item #1234T) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. A sample size is chosen such that the teabag does not restrict the swelling of the material, generally with dimensions smaller than the sealed bag area (about 2-inch by 2.5 inch). Three sample bags are tested for each material.

The sealed bags are submerged in a pan of 0.9% NaCl solution. After wetting, the samples remain in the solution for 60 minutes, at which time they are removed from the solution and temporarily laid on a non-absorbent flat surface.

The wet bags are then placed into the basket of a suitable centrifuge capable of subjecting the samples to a g-force of 350. (A suitable centrifuge is a Heraeus LABOFUGE 400, Heraeus Instruments, part number 75008157, available from Heraeus Infosystems GmbH, Hanau, Germany). The bags are centrifuged at 1600 rpm for 3 minutes (target g-force of 350). The bags are removed and weighed. The amount of fluid absorbed and retained by the material, taking into account the fluid retained by the bag material alone, is the Centrifugal Retention Capacity of the material, expressed as grams of fluid per gram of material.

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent article having a central region and two end regions, comprising:
   a liquid-permeable fluid receiving layer;
   an absorbent core; and
   a liquid-impermeable outer cover;
   wherein at least one of the fluid receiving layer, absorbent core and outer cover includes a flexible absorbent binder bound to a first substrate layer at predetermined elongated locations defining one or more elongated channels therebetween;
   the flexible absorbent binder being formed on the substrate layer at the predetermined elongated locations by crosslinking an absorbent binder composition on the substrate layer;
   the absorbent binder composition including a water-soluble ionic polymer capable of sufficient non-radiative crosslinking within about 10 minutes at a temperature not more than about 120° C., to reach an absorbent capacity of at least one gram per gram using the centrifuge retention capacity test.

2. The absorbent article of claim 1, wherein the absorbent core comprises the substrate layer and flexible absorbent binder bound to the substrate layer.

3. The absorbent article of claim 1, wherein the fluid receiving layer comprises the substrate layer and the flexible absorbent binder bound to the substrate layer.

4. The absorbent article of claim 1, wherein the outer cover comprises the substrate layer and the absorbent core comprises the flexible absorbent binder bound to the substrate layer.

5. The absorbent article of claim 1, further comprising a menses modifying agent combined with the flexible absorbent binder.

6. The absorbent article of claim 1, further comprising superabsorbent particles combined with the flexible absorbent binder.

7. The absorbent article of claim 1, comprising a sanitary napkin.

8. The absorbent article of claim 1, comprising a diaper.

9. The absorbent of claim 1, comprising a training pant.

10. The absorbent article of claim 1, comprising an adult incontinence garment.

11. The absorbent article of claim 1, comprising a medical absorbent article.

12. An absorbent article having selective folding during wear, comprising:
    a liquid-permeable fluid receiving layer;
    an absorbent core; and
    a liquid-impermeable outer cover;
    wherein at least one of the fluid receiving layer, absorbent core and outer cover includes a substrate layer and a flexible absorbent binder bound to the substrate layer at elongated locations defining one or more elongated channels therebetween;
    the flexible absorbent binder being formed on the substrate layer at the elongated locations by crosslinking an absorbent binder composition on the substrate layer at the elongated locations;
    the elongated locations comprising a plurality of stripes.

13. The absorbent article of claim 12, wherein the stripes are substantially parallel to each other and extend in a lateral direction.

14. The absorbent article of claim 13, wherein the laterally extending stripes cover an entire width of the absorbent core.

15. The absorbent article of claim 13, wherein the laterally extending stripes cover only part of a width of the absorbent core, further comprising a plurality of longitudinally extending stripes of flexible absorbent binder spaced from the laterally extending stripes.

16. The absorbent article of claim 12, comprising four of the stripes arranged to form a diamond shape.

17. The absorbent article of claim 12, wherein the flexible absorbent binder is combined with a menses modifying agent.

18. The absorbent article of claim 12, wherein the flexible absorbent binder is combined with superabsorbent particles.

19. The absorbent article of claim 12, wherein the flexible absorbent binder is formed on the substrate layer at the elongated locations by crosslinking an absorbent binder composition including about 15 to about 99.9% by mass monoethylenically unsaturated polymer units, about 0.1 to about 20% by mass ester units selected from the group consisting of acrylate and methacrylate ester units that include an alkoxysilane functionality, and zero to about 75% by mass of units selected from the group consisting of polyolefin glycol and polyolefin oxide units.

20. The absorbent article of claim 1, wherein the flexible absorbent binder is formed on the substrate layer at the elongated locations by crosslinking an absorbent binder composition including about 15 to about 99.9% by mass monoethylecnically unsaturated polymer units, about 0.1 to about 20% by mass ester units selected from the group consisting of actylate and methacrylate ester units that include an alkoxysilane functionality, and zero to about 75% by mass of units selected from the group consisting of polyolefin glycol and polyolefin oxide units.

21. The absorbent article of claim 1, wherein the flexible absorbent binder is bound around a periphery of the substrate to form a dam.

22. The absorbent article of claim 1, wherein the flexible absorbent binder is bound to elongated locations on the substrate defining a plurality of channels therebetween.

23. The absorbent article of claim 21, wherein the flexible absorbent binder is further bound to elongated locations on the substrate defining a plurality of channels therebetween.

24. The absorbent article of claim 23, wherein the channels include a relatively wide channel extending longitudinally in the central region, two longitudinally extending channels and two laterally extending channels surrounding the central region, and a plurality of radially extending channels in the two end regions.

25. The absorbent article of claim 24, wherein the radially extending channels become gradually narrower further away from the central region.

26. The absorbent article of claim 22, wherein the channels include a rectangular channel in the central region, and a plurality of radially extending channels commencing at the rectangular channel and terminating in each of the two end regions.

27. The absorbent article of claim 26, wherein the radially extending channels become gradually narrower further away from the central region.

28. The absorbent article of claim 22, wherein the elongated locations of flexible absorbent binder include a plurality of longitudinally extending stripes in the central region.

29. The absorbent article of claim 1, wherein the first substrate layer has first and second sides, and the flexible absorbent binder is bound at elongated locations on both sides.

30. The absorbent article of claim 29, wherein the elongated locations of flexible absorbent binder include a plurality of stripes on the first side and a plurality of stripes on the second side of the substrate.

31. The absorbent article of claim 30, wherein the stripes on the first side are staggered with respect to the stripes on the second side.

32. The absorbent article of claim 1, further comprising a second substrate layer, wherein the flexible absorbent binder is bound at one or more elongated locations to the first substrate layer and one or more elongated locations to the second substrate layer.

33. The absorbent article of claim 32, wherein the elongated locations on the first substrate layer include a plurality of stripes and the elongated locations on the second substrate layer include a plurality of stripes.

34. The absorbent article of claim 33, wherein the first substrate layer has first and second sides, and the elongated locations on the first substrate layer include a plurality of stripes on the first side and a plurality of stripes on the second side.

35. The absorbent article of claim 34, wherein the stripes on the second side of the first substrate layer are staggered with respect to the stripes on the first side of the first substrate layer and with respect to the stripes on the second substrate layer.

36. The absorbent article of claim 32, further comprising a third substrate layer, wherein the flexible absorbent binder is bound at one or more elongated locations to the third substrate layer.

37. The absorbent article of claim 36, wherein the elongated locations on the first substrate layer include a plurality of stripes, the elongated locations on the second substrate layer include a plurality of stripes, and the elongated locations on the third substrate layer include a plurality of stripes.

38. The absorbent article of claim 37, wherein distances between the stripes on the first substrate are wider than distances between the stripes on the second and third substrate layers.

39. The absorbent article of claim 37, wherein the stripes on the second substrate layer are staggered with respect to the stripes on the first and third substrate layers.

40. The absorbent article of claim 1, wherein the substrate layer has a substantially flat surface topography.

41. The absorbent article of claim 1, wherein the substrate layer has a three-dimensional surface topography including a plurality of semi-circular protrusions.

* * * * *

UNITED STATES PATENT AND TRADEMARK OFFICE
CERTIFICATE OF CORRECTION

PATENT NO. : 6,964,803 B2
DATED : November 15, 2005
INVENTOR(S) : Candace Dyan Krautkramer et al.

It is certified that error appears in the above-identified patent and that said Letters Patent is hereby corrected as shown below:

Column 21,
Line 7, delete "actylate" and insert -- acrylate --.

Signed and Sealed this

Seventh Day of February, 2006

JON W. DUDAS
*Director of the United States Patent and Trademark Office*